(12) United States Patent
Garrison et al.

(10) Patent No.: US 9,168,052 B2
(45) Date of Patent: *Oct. 27, 2015

(54) APPARATUS FOR PERFORMING AN ELECTROSURGICAL PROCEDURE

(71) Applicant: Covidien LP, Mansfield, MA (US)

(72) Inventors: David M. Garrison, Longmont, CO (US); Glenn A. Horner, Boulder, CO (US)

(73) Assignee: Covidien LP, Mansfield, MA (US)

( * ) Notice: Subject to any disclaimer, the term of this patent is extended or adjusted under 35 U.S.C. 154(b) by 291 days.

This patent is subject to a terminal disclaimer.

(21) Appl. No.: 13/853,259

(22) Filed: Mar. 29, 2013

(65) Prior Publication Data

US 2013/0226226 A1    Aug. 29, 2013

Related U.S. Application Data

(63) Continuation of application No. 12/792,051, filed on Jun. 2, 2010, now Pat. No. 8,409,247.

(51) Int. Cl.
  *A61B 17/29*    (2006.01)
  *A61B 18/14*    (2006.01)
  *A61B 18/00*    (2006.01)

(52) U.S. Cl.
  CPC ............. *A61B 17/29* (2013.01); *A61B 18/1445* (2013.01); *A61B 2018/0063* (2013.01)

(58) Field of Classification Search
  None
  See application file for complete search history.

(56) References Cited

U.S. PATENT DOCUMENTS

| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,250,056 A | 10/1993 | Hasson |
| D343,453 S | 1/1994 | Noda |
| 5,295,990 A | 3/1994 | Levin |
| D348,930 S | 7/1994 | Olson |
| D349,341 S | 8/1994 | Lichtman et al. |
| 5,359,993 A | 11/1994 | Slater et al. |

(Continued)

FOREIGN PATENT DOCUMENTS

| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Michael Peffley (57) ABSTRACT

A surgical instrument is provided and includes a housing having a shaft. An end effector assembly is operatively connected to a distal end of the shaft and has a pair of first and second jaw members one of which is movable with respect to the other. A heat activated drive assembly operably couples to an actuation mechanism that is operably associated with the forceps and configured to supply thermal energy to the heat activated drive assembly. The heat activated drive assembly operably coupled to movable jaw member and configured to impart movement of the movable jaw member when the actuation mechanism is activated.

20 Claims, 4 Drawing Sheets

(56) References Cited

U.S. PATENT DOCUMENTS

| | | |
|---|---|---|
| D354,564 S | 1/1995 | Medema |
| D358,887 S | 5/1995 | Feinberg |
| 5,454,378 A | 10/1995 | Palmer et al. |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,766,910 B2 | 8/2010 | Hixson et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,887,536 B2 | 2/2011 | Johnson et al. |
| 7,918,848 B2 | 4/2011 | Lau et al. |
| 7,951,150 B2 | 5/2011 | Johnson |
| 8,015,867 B2 | 9/2011 | Kerr et al. |
| D649,249 S | 11/2011 | Guerra |
| D649,643 S | 11/2011 | Allen, IV et al. |
| 8,112,871 B2 | 2/2012 | Brandt |
| 8,114,122 B2 | 2/2012 | Nau, Jr. |
| 8,133,254 B2 | 3/2012 | Dumbauld |
| 8,142,473 B2 | 3/2012 | Cunningham |
| 8,162,965 B2 | 4/2012 | Reschke |
| 8,187,273 B2 | 5/2012 | Kerr |
| D661,394 S | 6/2012 | Romero et al. |
| 8,197,479 B2 | 6/2012 | Olson et al. |
| 8,226,650 B2 | 7/2012 | Kerr |
| 8,251,994 B2 | 8/2012 | Mckenna et al. |
| 8,266,783 B2 | 9/2012 | Brandt |
| 8,277,446 B2 | 10/2012 | Heard |
| 8,277,447 B2 | 10/2012 | Garrison et al. |
| 8,282,634 B2 | 10/2012 | Cunningham |
| 8,287,536 B2 | 10/2012 | Mueller et al. |
| 8,292,886 B2 | 10/2012 | Kerr et al. |
| 8,715,277 B2 * | 5/2014 | Weizman ............... 606/27 |
| 2006/0217697 A1 | 9/2006 | Lau et al. |
| 2007/0173814 A1 | 7/2007 | Hixson et al. |
| 2007/0260242 A1 | 11/2007 | Dycus et al. |
| 2010/0023009 A1 | 1/2010 | Moses et al. |
| 2010/0087816 A1 | 4/2010 | Roy |
| 2010/0094271 A1 | 4/2010 | Ward et al. |
| 2010/0094287 A1 | 4/2010 | Cunningham |
| 2010/0100122 A1 | 4/2010 | Hinton |
| 2010/0130971 A1 | 5/2010 | Baily |
| 2010/0179543 A1 | 7/2010 | Johnson et al. |
| 2010/0179545 A1 | 7/2010 | Twomey et al. |
| 2010/0179546 A1 | 7/2010 | Cunningham et al. |
| 2010/0249769 A1 | 9/2010 | Nau, Jr. et al. |
| 2010/0280511 A1 | 11/2010 | Rachlin et al. |
| 2011/0015632 A1 | 1/2011 | Artale |
| 2011/0034918 A1 | 2/2011 | Reschke |
| 2011/0046623 A1 | 2/2011 | Reschke |
| 2011/0054468 A1 | 3/2011 | Dycus |
| 2011/0054471 A1 | 3/2011 | Gerhardt, Jr. |
| 2011/0054472 A1 | 3/2011 | Romero |
| 2011/0060333 A1 | 3/2011 | Mueller |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0077648 A1 | 3/2011 | Lee et al. |
| 2011/0077649 A1 | 3/2011 | Kingsley |
| 2011/0082494 A1 | 4/2011 | Kerr et al. |
| 2011/0087221 A1 | 4/2011 | Siebrecht et al. |
| 2011/0118736 A1 | 5/2011 | Harper et al. |
| 2011/0184405 A1 | 7/2011 | Mueller |
| 2011/0190653 A1 | 8/2011 | Harper |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin |
| 2011/0238066 A1 | 9/2011 | Olson |
| 2012/0150176 A1 | 6/2012 | Weizman |
| 2013/0150842 A1 | 6/2013 | Nau, Jr. |
| 2013/0178852 A1 | 7/2013 | Allen, IV |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 02617 | 12/2005 |
| DE | 20 2007 00931 | 8/2007 |
| DE | 20 2007 00916 | 10/2007 |
| DE | 20 2007 00931 | 10/2007 |
| DE | 20 2007 01623 | 3/2008 |
| DE | 19738457 | 1/2009 |
| DE | 10 2008 01840 | 7/2009 |
| EP | 1053719 | 11/2000 |
| EP | 1053720 | 11/2000 |
| EP | 1159926 | 12/2001 |
| EP | 1177771 | 2/2002 |
| EP | 1777771 | 2/2002 |
| JP | 61-501068 | 9/1984 |
| JP | 6-502328 | 3/1992 |
| JP | 65-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |

(56) References Cited

FOREIGN PATENT DOCUMENTS

| | | |
|---|---|---|
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 2005/110264 | 11/2005 |
| WO | WO 2006/021269 | 3/2006 |
| WO | WO 2008/040483 | 4/2008 |
| WO | WO 2008045348 | 4/2008 |
| WO | WO 2009039179 | 3/2009 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, 6/920/00, Thomas P. Ryan.
U.S. Appl. No. 12/336,970, filed Dec. 17, 2008, Paul R. Sremeich.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/663,317, filed Oct. 29, 2012, Unger.
U.S. Appl. No. 13/708,335, filed Dec. 7, 2012, Dumbauld.
U.S. Appl. No. 13/711,201, filed Dec. 11, 2012, Regadas.
U.S. Appl. No. 13/736,650, filed Jan. 8, 2013, McKenna.
U.S. Appl. No. 13/741,550, filed Jan. 15, 2013, Deborski.
U.S. Appl. No. 13/747,090, filed Jan. 22, 2013, Romero.
U.S. Appl. No. 13/747,167, filed Jan. 22, 2013, Romero.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/853,259, filed Mar. 29, 2013, Garrison.
U.S. Appl. No. 13/853,273, filed Mar. 29, 2013, Kerr.
U.S. Appl. No. 13/853,339, filed Mar. 29, 2013, Reschke.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.

(56) References Cited

OTHER PUBLICATIONS

Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

* cited by examiner

APPARATUS FOR PERFORMING AN ELECTROSURGICAL PROCEDURE

CROSS-REFERENCE TO RELATED APPLICATIONS

The present application is a continuation application of and claims the benefit of and priority to U.S. patent application Ser. No. 12/792,051 filed on Jun. 2, 2010 by Garrison et al., now U.S. Pat. No. 8,409,247, the entire contents of which is hereby incorporated by reference.

BACKGROUND

1. Technical Field

The present disclosure relates to an apparatus for performing an electrosurgical procedure. More particularly, the present disclosure relates to an electrosurgical apparatus including an end effector assembly having a pair of jaw members that provide a mechanical advantage at the end effector.

2. Description of Related Art

Electrosurgical instruments, e.g., electrosurgical forceps (open or closed type), are well known in the medical arts and typically include a housing, a handle assembly, a shaft and an end effector assembly attached to a distal end of the shaft. The end effector includes jaw members configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, cut, desiccate, and/or fulgurate tissue. Typically, one or more driving mechanisms, e.g., a drive assembly including a drive rod, is utilized to cooperate with one or more components operatively associated with the end effector to impart movement to one or both of the jaw members.

In certain instances, to facilitate moving the jaw members from an open position for grasping tissue to a closed position for clamping tissue (or vice versa) such that a consistent, uniform tissue effect (e.g., tissue seal) is achieved, one or more types of suitable devices may be operably associated with the electrosurgical forceps. For example, in some instances, one or more types of springs, e.g., a compression spring, may operably couple to the handle assembly associated with the electrosurgical forceps. In this instance, the spring is typically operatively associated with the drive assembly to facilitate actuation of a movable handle associated with the handle assembly to ensure that a specific closure force between the jaw members is maintained within one or more suitable working ranges.

In certain instances, the shaft may bend or deform during the course of an electrosurgical procedure. For example, under certain circumstances, a clinician may intentionally bend or articulate the shaft to gain desired mechanical advantage at the surgical site. Or, under certain circumstances, the surgical environment may cause unintentional or unwanted bending or flexing of the shaft, such as, for example, in the instance where the shaft is a component of a catheter-based electrosurgical forceps. More particularly, shafts associated with catheter-based electrosurgical forceps are typically designed to function with relatively small jaw members, e.g., jaw members that are configured to pass through openings that are 3 mm or less in diameter. Accordingly, the shaft and operative components associated therewith, e.g., a drive rod, are proportioned appropriately. That is, the shaft and drive rod are relatively small.

As can be appreciated, when the shaft is bent or deformed (either intentionally or unintentionally) the frictional losses associated with drive rod translating through the shaft are transferred to the spring in the housing, which, in turn, may diminish, impede and/or prevent effective transfer of the desired closure force that is needed at the jaw members. Moreover, the frictional losses may also lessen the operative life of the spring, which, in turn, ultimately lessens the operative life of the electrosurgical instrument.

An increased mechanical advantage and/or mechanical efficiency with respect to transferring the closure force(s) from the handle assembly to the jaw members may prove advantageous in the relevant art.

SUMMARY

The present disclosure provides a forceps. The forceps includes a housing having one or more shafts that extend therefrom and define a longitudinal axis therethrough. An end effector assembly is operatively connected to a distal end of the shaft and has a pair of first and second jaw members one of which being movable relative to the other from an open position wherein the first and second jaw members are disposed in spaced relation relative to one another, to a clamping position wherein the first and second jaw members cooperate to grasp tissue therebetween. A heat activated drive assembly operably couples to an actuation mechanism that is operably associated with the forceps and configured to supply thermal energy to the heat activated drive assembly. The heat activated drive assembly operably couples to one movable jaw member and is configured to impart movement of the one movable jaw member when the actuation mechanism is activated.

In embodiments, the heat activated drive assembly is configured to house an amount of one of a heat activated wax and shape memory alloy.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1A:
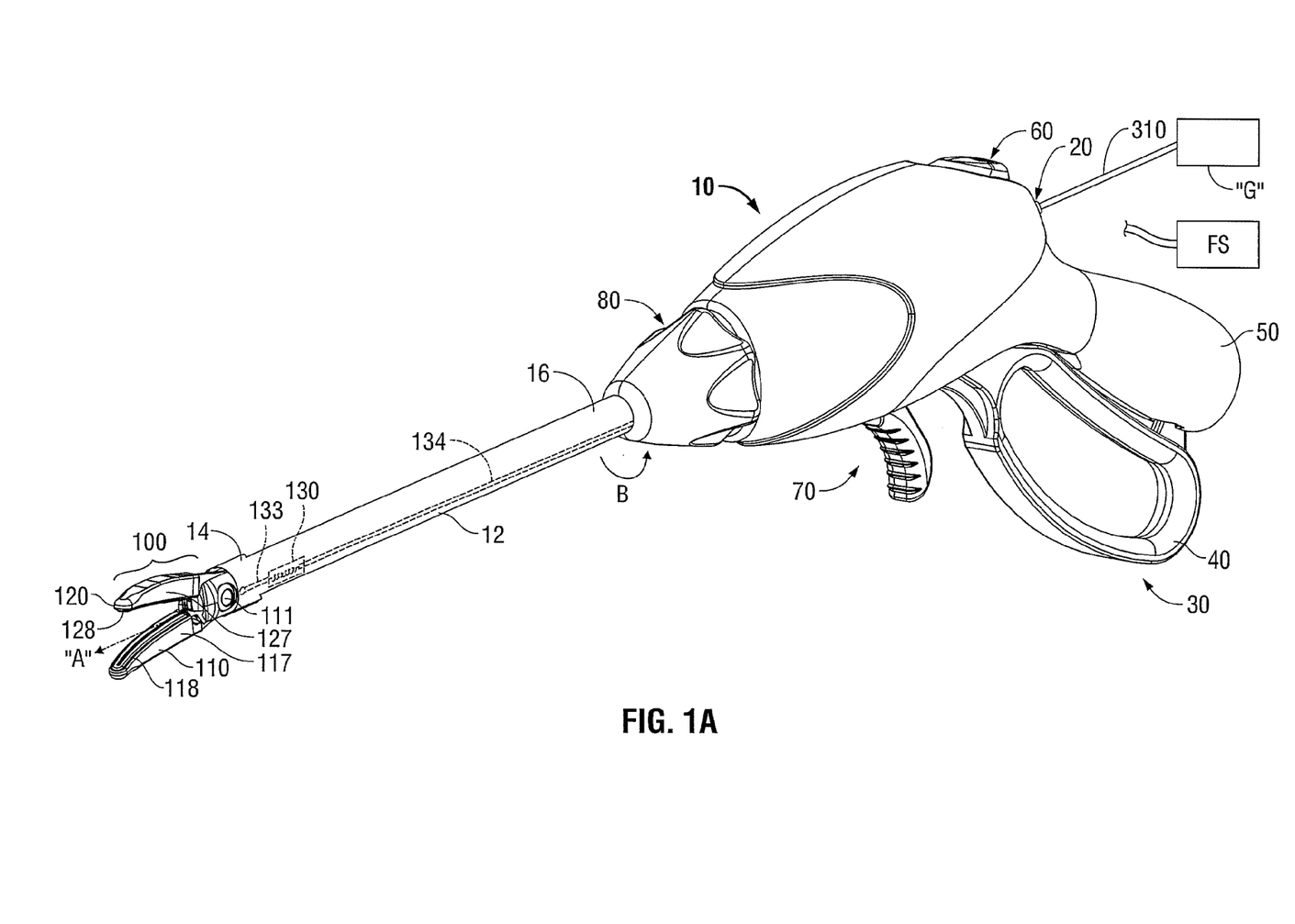
FIG. 1A is a side, perspective view of an endoscopic bipolar forceps showing an end effector assembly including jaw members according to an embodiment of the present disclosure.
Figure 1B:
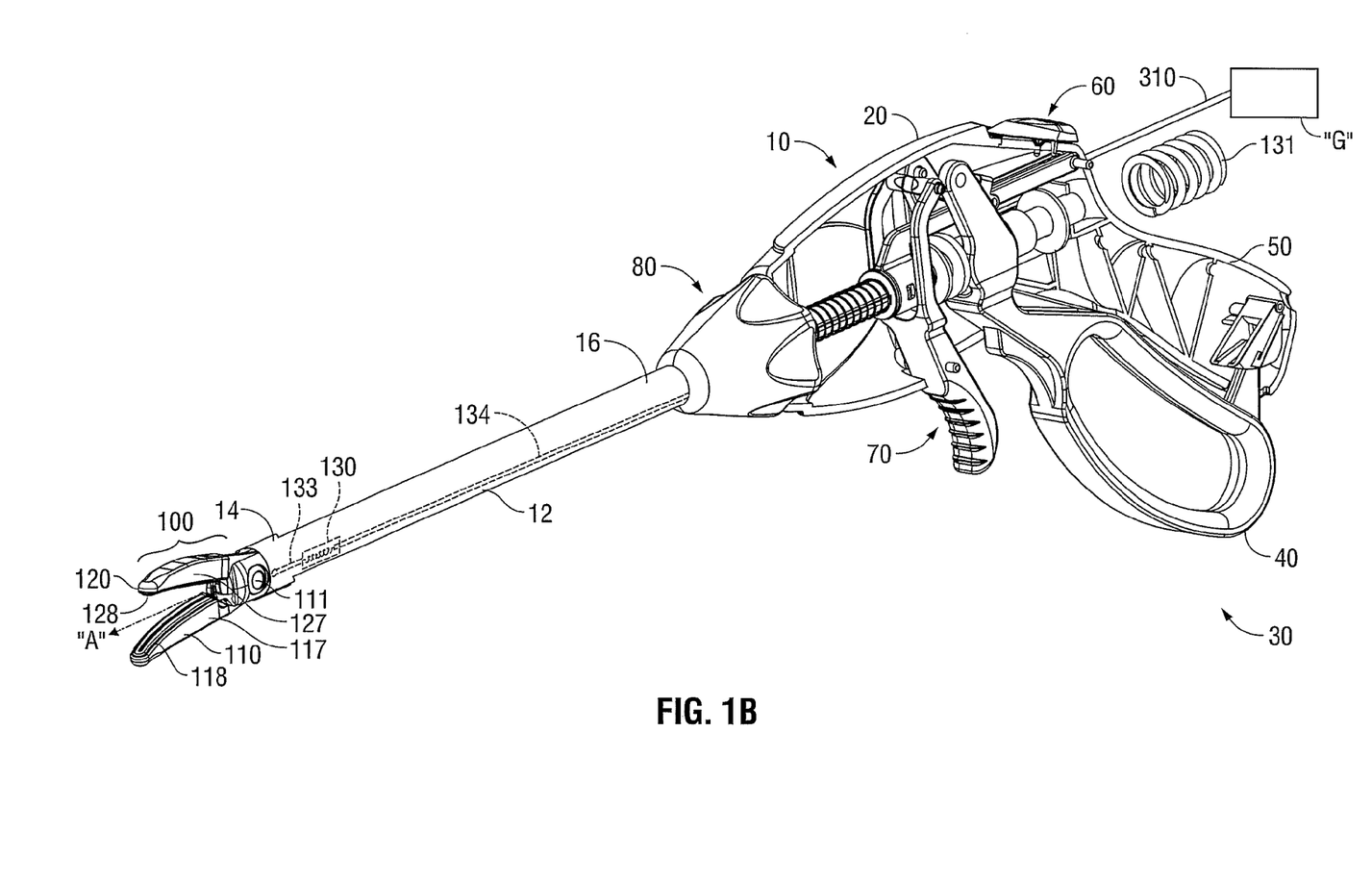
FIG. 1B is a side, perspective view of the endoscopic bipolar forceps depicted in FIG. 1A illustrating internal components associated with a handle assembly associated with the endoscopic bipolar forceps.

With reference to FIGS. 1A and 1B, an illustrative embodiment of an electrosurgical apparatus, e.g., a bipolar forceps 10 (forceps 10) is shown. Forceps 10 is operatively and selectively coupled to an electrosurgical generator "G" (generator "G") for performing an electrosurgical procedure. As noted above, an electrosurgical procedure may include sealing, cutting, fusing (i.e., joined but not sealed), cauterizing, coagulating, desiccating, and fulgurating tissue all of which may employ RF energy. The generator "G" may be configured for monopolar and/or bipolar modes of operation. Generator "G" may include or is in operative communication with a system (not shown) that may include one or more processors in operative communication with one or more control modules that are executable on the processor. The control module (not explicitly shown) may be configured to instruct one or more modules to transmit electrosurgical energy, which may be in the form of a wave or signal/pulse, via one or more cables (e.g., an electrosurgical cable 310) to the forceps 10.

Figure 2:
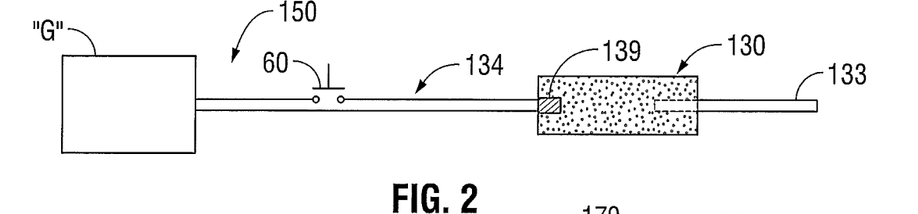
FIG. 2 is a schematic view illustrating an electrical configuration configured to actuate a drive assembly operably associated with the jaw members depicted in FIGS. 1A and 1B.

Forceps 10 is shown configured for use with various electrosurgical procedures and generally includes a housing 20, electrosurgical cable 310 that connects the forceps 10 to the generator "G", a handle assembly 30, a rotating assembly 80, an actuation mechanism 60, a trigger assembly 70, a heat activated drive assembly 130 (drive assembly 130) that includes a plunger 133, and an end effector assembly 100 that operatively connects to the drive assembly 130. End effector assembly 100 includes opposing jaw members 110 and 120 (FIGS. 1A and 1B) that mutually cooperate to grasp, seal and, in some cases, divide large tubular vessels and large vascular tissues. The drive assembly 130 is in operative communication with actuation mechanism 60 (see FIGS. 1A and 1B in combination with FIG. 2) for imparting movement of one or both of a pair of jaw members 110, 120 of end effector assembly 100, described in greater detail below. Conventional drive assemblies typically utilize one or more types of springs, e.g., a compression spring, to facilitate closing the jaw members 110 and 120. For illustrative purposes, a compression spring 131 (see FIG. 1B) is shown separated from the housing 20.

For a more detailed description of the forceps 10 including rotating assembly 80, trigger assembly 70, and electrosurgical cable 310 (including line-feed configurations and/or connections), reference is made to commonly owned U.S. patent application Ser. No. 11/595,194 filed on Nov. 9, 2006, now U.S. Patent Publication No. 2007/0173814.

With continued reference to FIGS. 1A and 1B, forceps 10 includes a shaft 12 that has a distal end 14 configured to mechanically engage the end effector assembly 100 and a proximal end 16 that mechanically engages the housing 20. In the drawings and in the descriptions that follow, the term "proximal," as is traditional, will refer to the end of the forceps 10 which is closer to the user, while the term "distal" will refer to the end that is farther from the user.

Handle assembly 30 includes a fixed handle 50 and movable handle 40. In one particular embodiment, fixed handle 50 is integrally associated with housing 20 and handle 40 is movable relative to fixed handle 50 for effecting one or more functions associated with the forceps 10. For example, in one particular embodiment, the movable handle 40 may be configured to provide electrosurgical energy to one or more operative components, e.g., end effector 100, associated with the forceps 10.

Figure 3A:
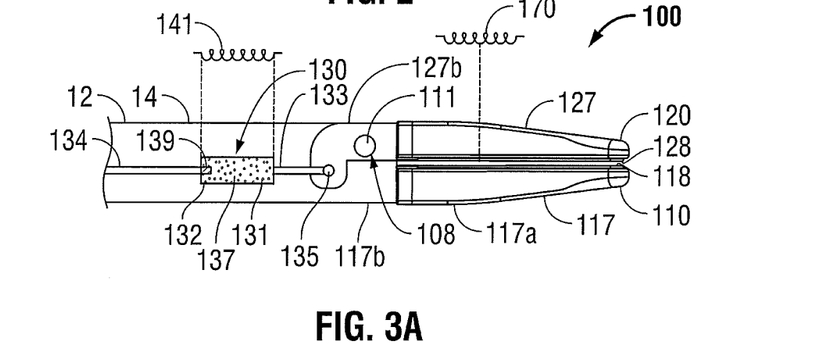
FIGS. 3A and 3B are schematic views of the jaw members depicted in FIGS. 1A and 1B.

Actuation mechanism 60 is operably associated with the forceps 10 and is in electrical communication with the drive assembly 130. More particularly, when the actuation mechanism 60 is activated, one or both of the jaw members, e.g., jaw member 120, is caused to move from a closed or clamped position to an open position (or, in some instances, from an open to closed position). Actuation mechanism 60 is operably disposed at a proximal end of the housing 20 and is in electrical communication with generator "G," see FIG. 2, for example. Actuation mechanism 60 may be any suitable type of actuation mechanism, including but not limited to a button (e.g., a push-button 60), switch, lever, handle (e.g., a movable handle 40) or the like. In the illustrated embodiment, actuation mechanism 60 is in the form of a push-button 60. Push-button 60 is configured to actuate the drive assembly 130. More particularly, push-button 60 serves as a switch and is configured to provide current to the drive assembly 130 such that a thermal effect is caused thereto, described in greater detail below. Push-button 60 is in electrical communication with a lead 134 that is part of an electrical circuit 150 (FIGS. 2-3B) and in electrical communication with drive assembly 130 (or one or more components operably associated therewith). In the illustrated embodiment, the lead 134 is bundled with one or more other leads and/or wires that are disposed within the cable 310. When push-button 60 is pressed, current is allowed to flow to drive assembly 130, or component associated therewith, e.g., a heating element or filament 139. The amount of current and other attributes associated with the current that is utilized to activate the drive assembly 130 may be adjusted to achieve a desired effect at the drive assembly 130. For example, the greater the amount of current that flows to the drive assembly 130, the faster the drive assembly 130 moves one or both of the jaw members, e.g., jaw member 120, and/or the greater the clamping force between the jaw members 110 and 120. Moreover, the time that current is provided to the drive assembly 130 determines how long the drive assembly 130 maintains the jaw member 120 in the open (or closed) configuration.

Figure 3B:
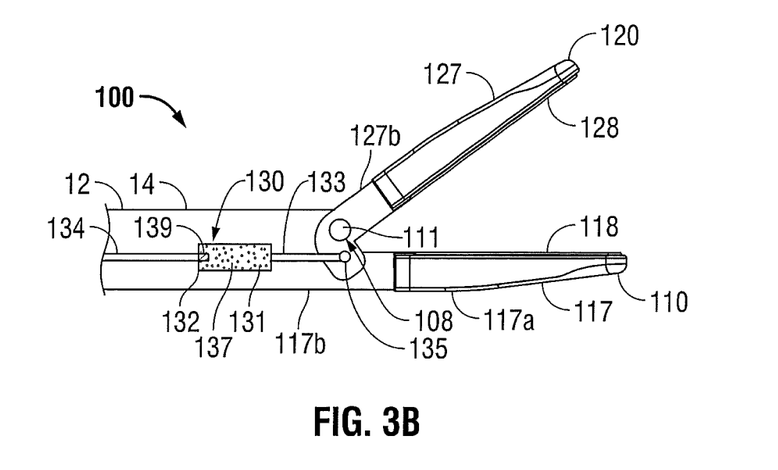

With reference now to FIGS. 3A and 3B, drive assembly 130 is operably disposed adjacent distal end 14 of the shaft 12 and the end effector 100. Alternatively, the drive assembly 130 may be disposed anywhere in the forceps 10 deemed advantageous for the purposes described herein. More particularly, drive assembly 130 is secured to an internal frame associated with the shaft 12 by any suitable securement methods including, but not limited to linkage, pins, stops, welds, adhesive, fastener, etc. Drive assembly 130 is configured to impart movement of one or both of the jaw members 110 and 120. To this end, drive assembly 130 includes a main housing 131 of suitable proportion. Main housing 131 is configured to house one or more operative components associated with the drive assembly 130. In the illustrated embodiment, the main housing 131 includes therein or is made from a heat activatable wax 137, e.g., paraffin wax. In certain embodiments, main housing 131 may include therein or may be made from gas, liquid, or any heat expandable/contactible material. The main housing 131 is configured such that when the heat activatable wax 137 is heated, a plunger 133 that is operably disposed within the main housing is caused to translate distally. To this end, main housing 131 is in electrical communication with the generator "G" via lead 134. More particularly, lead 134 is operably coupled to a proximal end 132 of the main housing 131 via one or more suitable coupling methods, e.g., lead 134 is soldered to proximal end 132.

Heating element or filament 139 is operably disposed within the main housing 131 and is in electrical communication with the lead 134. More particularly, the filament 139 is operably secured, e.g., via a solder joint or other suitable connection, to the main housing 131 adjacent the proximal end 132 and in operative communication with the heat activatable wax 137. When push-button 60 is pressed, current from the generator "G" flows to filament 139 via the lead 134. The current heats up the filament 139 such that the heat activatable wax 137 causes plunger 133 to move, e.g., translate distally.

While the drive assembly 130 has been described as including a filament 139, it is within the purview of the present disclosure that the drive assembly 130 may function without the filament 139. For example, the main housing 131 may be coupled to the lead 134 in a manner that provides for the main housing 131 to function as the filament 139. In this instance, as current heats up the main housing 131 the heat activatable wax 137 causes plunger 133 to move, e.g., translate distally.

Plunger 133 is dimensioned to translate within the main housing 131 of the drive assembly 130 from an initial position, wherein jaw member 120 is in the clamping position (FIG. 3A) to a subsequent position, wherein the jaw member 120 is in the open configuration (FIG. 3B). A distal end 135 of the plunger 133 operably couples to a proximal end of the jaw member 120 via one or more suitable coupling methods. In the illustrated embodiment, the distal end 135 is coupled to a proximal end 127b (FIG. 3A) of the jaw member 120 via a pin joint. Plunger 133 is configured such that in the initial position, i.e., the clamped position, the jaw member 120 provides the necessary closure force at the jaw members 110 and 120 for sealing tissue, e.g., in the range of about 3 kg/cm$^2$ to about 16 kg/cm$^2$.

In certain embodiments, to facilitate cooling of the housing 131 and/or filament 139, a coil 141 of suitable proportion may be operably coupled to the main housing 131 and may be configured to provide a path for one or more coolants around an exterior of the housing 131. For illustrative purposes, the coil 134 is shown separated from the main housing 131. Coil 134 supplies a chilled coolant that is configured to rapidly cool the "heated" main housing 131, filament 139 and/or heat activatable wax 137 to facilitate moving the jaw member 120 back to the clamping position. Other methods for cooling the main housing 131 may include convection, conduction, and/ or radiation to surrounding air or surrounding material.

In the instance where a coil 141 is provided, the forceps 10 may be in fluid communication with a fluid source "FS" (FIG. 1A) that includes a circulating pump, reservoir, one or more hoses, etc. Fluid sources "FS" are well known in the art and will not be described in further detail.

With continued reference to FIGS. 3A and 3B, jaw members 110, 120 are operatively and pivotably coupled to each other and located adjacent the distal end 14 of shaft 12. Respective electrically conductive seal plates 118 and 128 are operably supported on and secured to respective jaw housings 117 and 127 of respective the jaw members 110 and 120, described in greater detail below. For the purposes herein, jaw members 110 and 120 include jaw housings 117 and 127 that are configured to support sealing plates 118 and 128, respectively.

Jaw members 110 and 120 including respective jaw housings 117 and 127, and operative components associated therewith may be formed from any suitable material, including but not limited to metal, metal alloys, plastic, plastic composites, etc. In illustrated embodiment, jaw members 110 and 120 are formed from metal. Jaw members 110 and 120 are substantially identical to each other, and, in view thereof, and so as not to obscure the present disclosure with redundant information, the operative components associated with the jaw housing 117 are described in further detail with respect to jaw member 110, and only those features distinct to jaw member 120 and jaw housing 127 will be described hereinafter.

A distal end 117a of the jaw housing 117 of jaw member 110 is configured to securely engage the electrically conductive seal plate 118. A portion of a proximal end 117b of the jaw member 110 is operably secured to the distal end 14 of the shaft 12. In the illustrated embodiment, jaw member 110 is stationary. That is, jaw member 110 does not move with respect to the shaft 12 and/or jaw member 120.

Unlike jaw member 110, jaw member 120 is movable. Jaw member 120 pivotably couples to jaw member 110 via a pivot pin 111. Proximal end 127b includes a generally "L" shaped lever arm. This "L" shape facilitates pivoting of the jaw member 120 when the plunger 133 is translated distally. In embodiments, one or more cam slots (not shown) may be operably disposed on the plunger 133 to facilitate rotational movement thereof.

An opening 108 is defined in and extends through the each of the jaw housing 117 and 127 and is configured to receive a pivot pin 111. Opening 108 is shown engaged with pivot pin 111 and as such is not explicitly visible.

In an assembled configuration each of the jaw members 110 and 120 are positioned in side-by-side relation. Pivot pin 111 is positioned within the openings associated with each of the jaw members 110 and 120. Pivot pin 111 provides a point of pivot for jaw member 120. Once assembled, the jaw members 110 and 120 may be pivotably supported at the distal end 14 of the shaft 12 by known methods, such as, for example, by the method described in commonly-owned U.S. Patent Application publication No. 2007/0260242, filed Jul. 11, 2007.

In use, initially jaw members 110 and 120 are biased in a closed configuration (or, in some instances, a normally open configuration) under the force provided by the plunger 133 (FIG. 3A). Push-button 60 is pressed, which, in turn, causes current to flow to the lead 134 and the filament 139. The current causes the filament 139 to "heat-up," which, in turn, causes the heat activatable wax 137 to "heat-up." Heating the heat activatable wax 137 causes the plunger 133 to translate distally. Distal translation of the plunger 133 causes the jaw member 120 to pivot about the pivot pin 111. Plunger 133 is configured to translate a predetermined distance that corresponds to a predetermined opening or moving of the jaw member 120. Based on a specific surgical procedure, the plunger 133 is configured to maintain the jaw member 120 in the open configuration for a predetermined amount of time or, alternatively, as long as a user desires thru real-time control. Tissue is positioned between the jaw members 110 and 120, and jaw member 120 subsequently moves back to the closed or clamped position. The combination of a drive assembly 130 with a heat activatable wax disposed therein and a plunger 133 provides an additional mechanical advantage at the jaw members 110 and 120 and reduces the frictional losses that are typically associated with conventional forceps when a drive rod is translated within a shaft to make the necessary closure force to seal tissue, e.g., the required closure force lower due to the position of the by the drive assembly 130 at the distal end 14 of the shaft 12 than at the proximal end 16 of the shaft 12, esp., in embodiments involving longer and non-linear shafts.

Figure 4A:
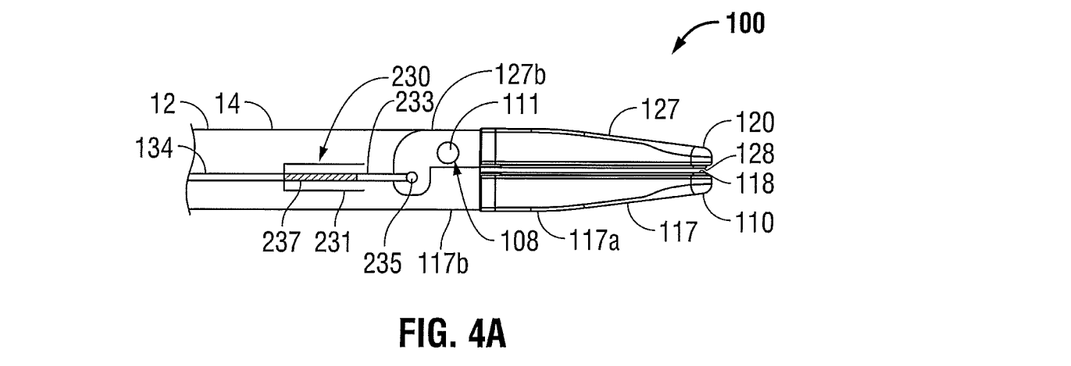
FIGS. 4A and 4B are schematic views of jaw members according to an alternate embodiment of the present disclosure.
Figure 4B:
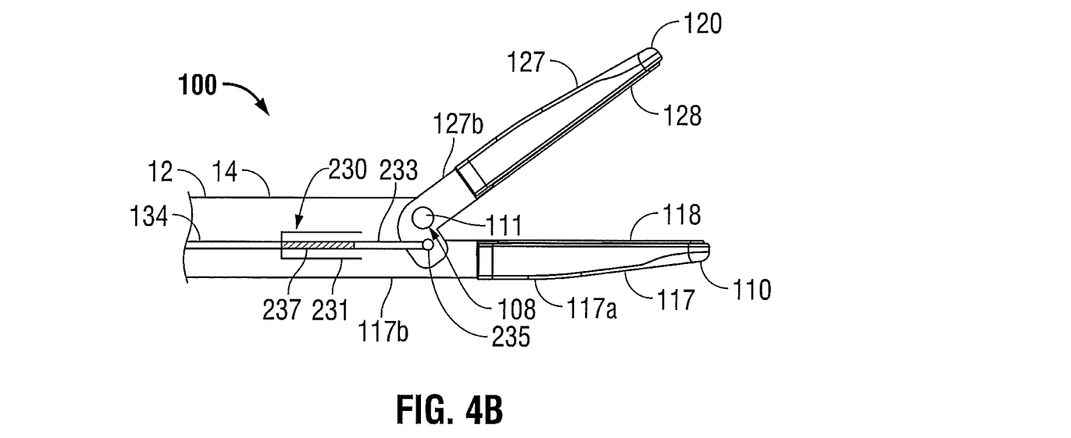

With reference to FIGS. 4A and 4B, a drive assembly 230 that is configured for use with the forceps 10 including an end effector 100 is illustrated. Drive assembly 230 is substantially similar to drive assembly 130. In view thereof, only those features that are unique to drive assembly 230 are described hereinafter.

Unlike drive assembly 130, drive assembly 230 includes a main housing 231 that includes therein a predetermined amount or volume of shape memory alloy 237, e.g., Nitinol. The main housing 231 is configured such that when the shape memory alloy 237 is heated, a plunger 233 (linkage or the like) that is operably disposed within the main housing 231 and in operative communication with the shape memory alloy 237 is caused to translate distally. To this end, main housing 231 is in electrical communication with the generator "G" via lead 134. Lead 134 is configured to function as described above with respect to drive assembly 230.

Figure 5:
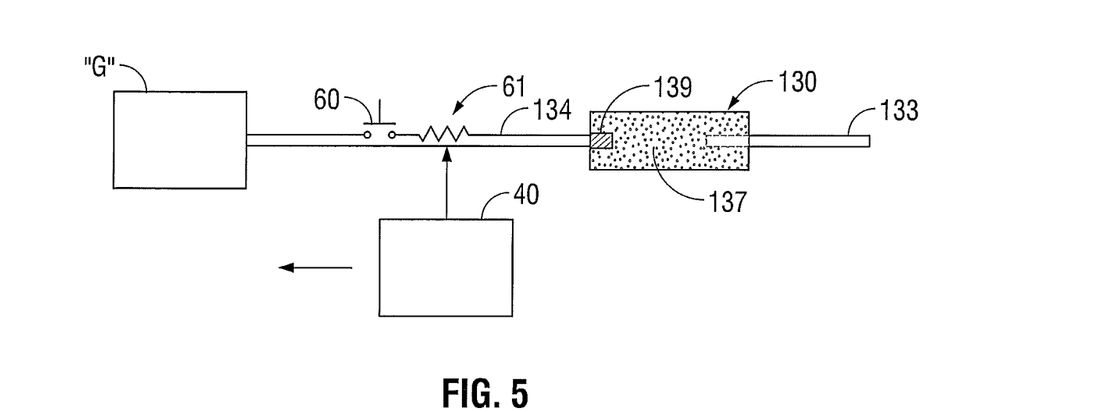
FIG. 5 is a schematic view illustrating an electrical configuration that is configured for use with a drive assembly operably associated with the jaw members depicted in FIGS. 1A and 1B.

The predetermined amount or volume of shape memory alloy 237 is formed into a generally elongated configuration (or any shape capable of producing the desired effects described herein, e.g., helix, bellows, linear, "u-shape," bent, wavy, etc.) and is operably disposed within the main housing 231. The elongated configuration of shape memory alloy 237 is in electrical communication with the lead 134. More particularly, the elongated configuration of shape memory alloy 237 is operably secured, e.g., via a solder joint, pin, weld, linkage, fastener, etc., to the main housing 231 adjacent the proximal end thereof. The elongated configuration of shape memory alloy 237 includes a cold forged state that corresponds to an expanded position (FIG. 5A). When push-button 60 is pressed, current from the generator "G" flows to the elongated configuration of shape memory alloy 237 via the lead 134. The current heats up the elongated configuration of shape memory alloy 237 such that the elongated configuration of shape memory alloy 237 transitions from the cold forged state to the "recovered state", i.e., expanded position, which, in turn, causes the plunger to translate distally.

A plunger 233 is dimensioned to translate within the main housing 231 of the drive assembly 230 from an initial position, wherein jaw member 120 is in the clamping position (FIG. 4A) to a subsequent position, wherein the jaw member 120 is in the open configuration (FIG. 4B). A distal end 235 of the plunger 233 operably couples to a proximal end of the jaw member 120 via one or more suitable coupling methods, including but not limited to a pin joint. Plunger 233 is configured such that in the initial position, i.e., the clamped position, the jaw member 120 provides the necessary closure force at the jaw members 110 and 120 for sealing tissue, e.g., in the range of about 3 kg/cm² to about 16 kg/cm².

In certain instances, a filament 139, such as the one described above with respect to drive assembly 130, may be operably coupled to the main housing 231. In this instance, the filament 139 may operably couple to the elongated configuration of shape memory alloy 237 via one of the aforementioned coupling methods, e.g., brazing.

In certain embodiments, the shape memory alloy 237 may serve as a resistive heating element or it may have a heating element wrapped around or bonded to it.

In certain embodiments, to facilitate cooling of the housing 231 and/or the elongated configuration of shape memory alloy 237, coil 141 may be operably coupled to the main housing 231 and may be configured to provide a path for one or more coolants around an exterior of the housing 231.

In use, initially jaw members 110 and 120 are biased in a closed configuration (or, in some instances, an open configuration) under the force provided by the plunger 233 (FIG. 4A). Push-button 60 is pressed, which, in turn, causes current to flow to the lead 234 and the elongated configuration of shape memory alloy 237. The current causes the elongated configuration of shape memory alloy 237 to "heat-up," which, in turn, causes the plunger 233 to translate distally. Distal translation of the plunger 233 causes the jaw member 120 to pivot about the pivot pin 111 (FIG. 4B). Plunger 233 is configured to translate a predetermined distance that corresponds to a predetermined opening or moving of the jaw member 120. Based on a specific surgical procedure, the plunger 233 is configured to maintain the jaw member 120 in the open configuration for a predetermined amount of time or, alternatively, as long as a user desires thru real-time control. Tissue is positioned between the jaw members 110 and 120, and jaw member 120 subsequently moves back to the closed or clamped position. The combination of a drive assembly 230 with an elongated configuration of a shape memory alloy 237 that is in operative communication with a plunger 233 provides an additional mechanical advantage at the jaw members 110 and 120 and reduces the frictional losses that are typically associated with conventional forceps when a drive rod is translated within a shaft to make the necessary closure force to seal tissue, e.g., the closure force is offloaded and/or diminished by the drive assembly 230.

From the foregoing and with reference to the various figure drawings, those skilled in the art will appreciate that certain modifications can also be made to the present disclosure without departing from the scope of the same. For example, one or more types of resilient members 170 (FIG. 3A) may be operably associated with one or both of the jaw housings 117 and 127 and may be utilized to facilitate moving one or both of the jaw members, e.g., jaw member 120, back to the closed or clamped position and to cooperate with the drive assembly 130 to provide the necessary closure force on the jaw members 110 and 120 for sealing tissue, e.g., in the range of about 3 kg/cm² to about 16 kg/cm². Suitable resilient members 170 (or other suitable device) may include, but are not limited to, torsion springs, leaf springs, coil springs, gas pistons, bladders, foam rubber, elastomers, etc. Moreover, the resilient member 170 may serve to prevent excessive forces developing on the jaw members 110 and 120 when the jaw members 110 and 120 are clamped on large or small vessels.

It is contemplated that movable handle 40 of handle assembly 30 may be operably coupled to the drive assembly 130, which, together, are configured to electromechanically cooperate to control a rate of movement of one or both of the jaw members 110 and 120. More particularly, movable handle 40 may be operably coupled to a current control device 61 (e.g., an electromechanical switch, electronic control system, a relay, a solenoid, a potentiometer, a rheostat, a variable resistor, etc.) that is in electrical communication with push-button 60 via lead 134, see FIG. 5, for example. The current control device 61 is configured to control current flow to the drive assembly 130 (FIG. 4). In this instance, movement of the movable handle 40 alters and/or varies the amount of current flow to the drive assembly 130. For example, in an embodiment, the current control device 61 may be a potentiometer 61 that is in electromechanical communication with movable handle 40. In this instance, movable handle 40 may be configured such that proximal movement thereof increases resistance of the potentiometer 61, which, in turn, for a given voltage, causes the current to the drive assembly to decrease, which, in turn, decreases how quickly the filament 139, and thus the heat activatable wax 137 (or shape memory alloy 237), heats up. As can be appreciated, controlling the rate (or temperature) at which the heat activatable wax 137 heats up may prove advantageous during an electrosurgical procedure.

It is contemplated that the actuation mechanism may be integrated into the movable handle 40 and/or trigger 70.

It is contemplated that the actuation mechanism may be actuated automatically when tissue is sensed. In this instance, one or more sensors may be operably associated with the forceps 10 and/or other component operably associated therewith, e.g., one or both of the jaw members 110 and 120.

While the jaw members 110 and 120 have been described in detail herein as being movable from an initially closed configuration to the open configuration, it is within the purview of the present disclosure that the jaw members 110 and 120 may be movable from an initially open or "neutral" configuration to the closed configuration. This of course will depend on the ultimate needs of a user.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
an end effector assembly having a pair of first and second jaw members at least one of which being movable relative to the other from an open position wherein the first and second jaw members are disposed in spaced relation relative to one another, to a clamping position wherein the first and second jaw members cooperate to grasp tissue therebetween;
an actuation mechanism; and
a drive assembly operably coupled to the actuation mechanism and including at least one heat activatable component configured to advance a plunger coupled to the at least one movable jaw member to impart movement of the at least one movable jaw member when the actuation mechanism is activated.

2. A forceps according to claim 1, wherein the drive assembly is configured to bias the jaw members in the clamping position and provide a closure force on tissue positioned between the first and second jaw members when the actuation mechanism is not activated.

3. A forceps according to claim 1, wherein the drive assembly is in electrical communication with the actuation mechanism.

4. A forceps according to claim 1, wherein the actuation mechanism is a push-button.

5. A forceps according to claim 1, wherein the drive assembly is operably disposed adjacent the end effector.

6. A forceps according to claim 1, wherein the drive assembly includes a housing that is configured to support a predetermined amount of heat activatable wax.

7. A forceps according to claim 6, wherein the plunger is operably disposed within the housing and configured to impart movement of the at least one moveable jaw to the open position when the heat activatable wax is heated.

8. A forceps according to claim 1, further comprising a fluid source configured to supply coolant to the drive assembly to facilitate moving the at least one movable jaw member back to the clamping position.

9. A forceps according to claim 6, wherein the at least one movable jaw member includes a generally curved proximal end that operably couples to the plunger of the drive assembly.

10. A forceps according to claim 1, wherein a resilient member is operably coupled to the at least one movable jaw member and configured to facilitate movement thereof back to the clamping position.

11. A forceps according to claim 10, wherein the resilient member is selected from the group consisting of compression spring, torsion spring and leaf spring.

12. A forceps according to claim 1, further comprising movable handle that is operably coupled to the drive assembly and configured to electromechanically cooperate with the drive assembly to control a rate of movement of one or both of the first and second jaw members.

13. A forceps according to claim 12, wherein the movable handle is operably coupled to a current control device that is in electrical communication with the actuation mechanism.

14. A forceps according to claim 13, wherein the current control device is selected from the group consisting of an electromechanical switch, a relay, a solenoid, a potentiometer, a rheostat and a variable resistor.

15. A forceps according to claim 13, wherein the current control device is configured to control current flow to the drive assembly when the movable handle is moved in one of a proximal or distal direction.

16. A forceps according to claim 13, wherein movement of the movable handle results in one of increasing and decreasing a resistance associated with the current control device such that, for a given voltage, current flow to the drive assembly is one of increased and decreased, wherein an increase in current to the drive assembly increases a temperature associated therewith and a decrease in current to the drive assembly decreases the temperature associated therewith.

17. A forceps according to claim 1, wherein the drive assembly includes a housing that is configured to support a shape memory alloy.

18. A forceps according to claim 17, wherein the plunger is operably disposed within the housing and configured to impart movement of the at least one moveable jaw to the open position when the shape memory alloy is heated.

19. A forceps according to claim 17, wherein the shape memory alloy is Nitinol.

20. A forceps according to claim 17, wherein the shape memory alloy includes a generally elongated shape.

* * * * *